United States Patent [19]

Denzel et al.

[11] 4,271,157
[45] Jun. 2, 1981

[54] IMIDAZOLE DERIVATIVES OF 7-[(2-AMINO-4-THIAZOLYL)-OXIMINO] CEPHALOSPORINS

[75] Inventors: Theodor Denzel, Regensburg; Hermann Breuer, Schoenhofen, both of Fed. Rep. of Germany

[73] Assignee: E. R. Squibb & Sons, Inc., Princeton, N.J.

[21] Appl. No.: 125,801

[22] Filed: Feb. 28, 1980

[51] Int. Cl.³ .................. A61K 31/545; C07D 501/56
[52] U.S. Cl. ...................................... 424/246; 544/22; 544/23; 544/25; 544/27; 544/28; 548/194
[58] Field of Search .................. 544/28, 22, 23, 25, 544/27; 424/246

[56] References Cited

U.S. PATENT DOCUMENTS

| 4,098,888 | 7/1978 | Ochiai et al. | 544/28 |
| 4,152,432 | 5/1979 | Heynes et al. | 544/28 |
| 4,166,115 | 8/1979 | Takaya et al. | 544/28 |

FOREIGN PATENT DOCUMENTS 2714880 10/1978 Fed. Rep. of Germany .
2716677 10/1978 Fed. Rep. of Germany .

Primary Examiner—Paul M. Coughlan, Jr.
Attorney, Agent, or Firm—Lawrence S. Levinson; Dale Lovercheck

[57] ABSTRACT

A compound of the formula

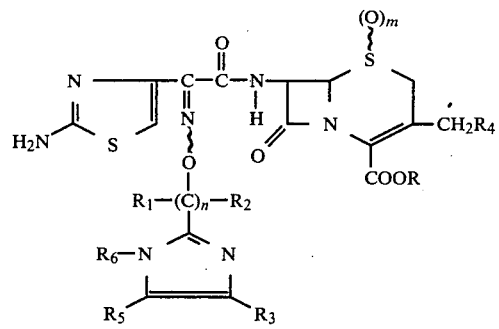

wherein
R is hydrogen, alkali metal,

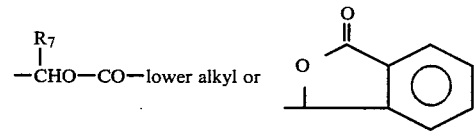

$R_1$ is hydrogen or methyl;
$R_2$ is hydrogen or methyl;
$R_3$ is hydrogen or methyl;
$R_4$ is hydrogen, —OCONH$_2$,

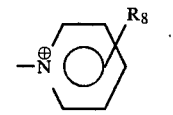

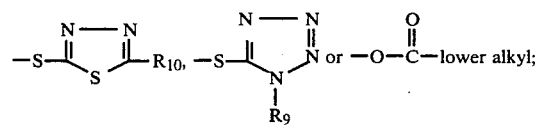

$R_5$ is hydrogen or methyl;
$R_6$ is hydrogen, methyl, benzyl or acetyl;
$R_7$ is hydrogen or lower alkyl;
$R_8$ is hydrogen or —CONH$_2$;
$R_9$ is hydrogen, lower alkyl,

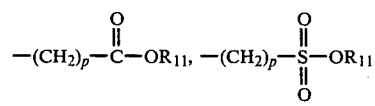

or —(CH$_2$)$_p$—N—(lower alkyl)$_2$;
$R_{10}$ is hydrogen or lower alkyl;
$R_{11}$ is hydrogen, sodium or potassium;
n is 1, 2, 3 or 4;
m is 0, 1 or 2;
p is 1, 2, 3 or 4.

12 Claims, No Drawings

IMIDAZOLE DERIVATIVES OF 7-[(2-AMINO-4-THIAZOLYL)-OXIMINO] CEPHALOSPORINS

BACKGROUND OF THE INVENTION

Hoechst in German Offenlegungsschrift No. 2,714,880 disclose antibacterially active cephalosporins including those of the formula

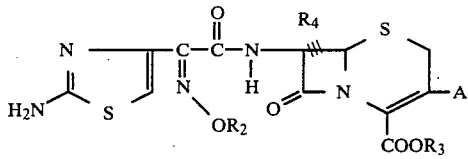

wherein $R_3$ is hydrogen; $R_4$ is hydrogen or alkoxy; A is various 3-position substituents; and $R_2$ is defined as alkyl of 1 to 4 carbons, for example methyl, having one or more substituents.

Hoechst in German Offenlegungsschrift No. 2,716,677 disclose antibacterially active cephalosporins including those of the formula

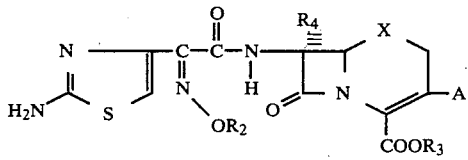

wherein X is an α- or β- —SO, or an $SO_2$ group; $R_4$ is hydrogen or alkoxy; A is various 3-position substituents; and $R_2$ is defined as an alkyl of 1 to 4 carbons, for example methyl, having one or more substituents.

Takaya et al. U.S. Pat. No. 4,166,115 disclose 3,7-disubstituted-3-cephem-4-carboxylic acid compounds of the general formula:

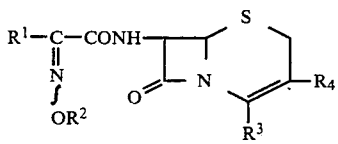

in which $R_1$ may be a group of the formula:

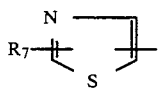

wherein $R^7$ is amino or protected amino; $R_2$ is an aliphatic hydrocarbon group which may have suitable substituents such as various heterocyclic groups, $R_3$ is carboxy or protected carboxy, and $R_4$ is methyl, acyloxymethyl, hydroxymethyl, formyl or a substituted heterocyclicthiomethyl group.

Heynes et al. in U.S. Pat. No. 4,152,432 discloses compounds of the formula:

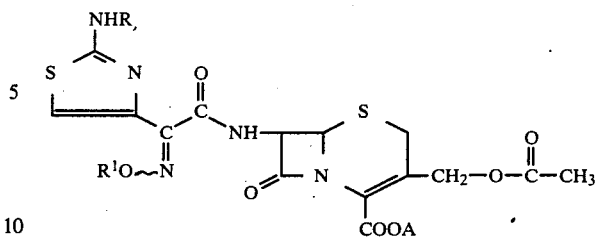

wherein $R^1$ is selected from the group consisting of hydrogen, alkyl of 1 to 4 carbon atoms, alkenyl and alkynyl of 2 to 4 carbon atoms and groups easily removable by acid hydrolysis or hydrogenolysis.

Ochiai et al. in U.S. Pat. No. 4,098,888 discloses compounds of the formula:

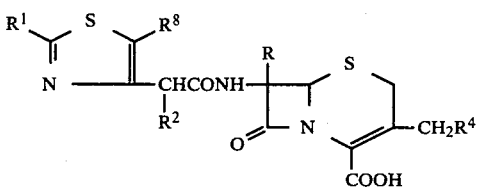

wherein $R_2$ represents amino or hydroxyl group or a group convertible into these groups.

SUMMARY OF THE INVENTION

This invention is directed to cephalosporins of the formula

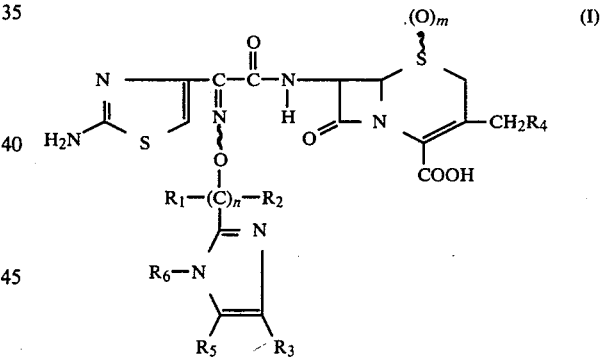

wherein
R is hydrogen, alkali metal,

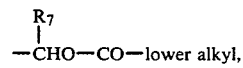

$Si(CH_3)_3$, p-methoxybenzyl, diphenylmethyl, benzyl, trichloroethyl,

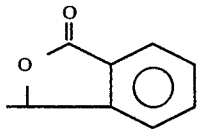

or lower alkyl;
$R_1$ and $R_2$, $R_3$ and $R_5$ are independently selected from hydrogen and methyl;

$R_4$ is hydrogen, —OCONH$_2$, $$-\overset{\oplus}{N}\underset{}{\bigcirc}R_8 \quad , \quad -S-\underset{S}{\overset{N-N}{\bigcirc}}-R_{10},$$

$$-S-\underset{\underset{R_9}{|}}{\overset{N----N}{\bigcirc}}\overset{N}{\underset{}{}}\quad \text{or} \quad -O-\overset{O}{\underset{||}{C}}-\text{lower alkyl};$$

$R_6$ is hydrogen, methyl, benzyl or acetyl;
$R_7$ is hydrogen or lower alkyl;
$R_8$ is hydrogen or —CONH$_2$;
$R_9$ is hydrogen, lower alkyl, $$-(CH_2)_p-\overset{O}{\underset{||}{C}}-OR_{11}, \quad -(CH_2)_p-\overset{O}{\underset{\underset{O}{||}}{S}}-OR_{11}$$

or —(CH$_2$)$_p$—N—(lower alkyl)$_2$;
$R_{10}$ is hydrogen or lower alkyl;
$R_{11}$ is hydrogen, sodium or potassium;
n is 1, 2, 3 or 4;
m is 0, 1 or 2;
p is 1, 2, 3 or 4.

When $R_4$ is pyridinium or carbamoyl substituted pyridinium, the compounds can be structurally represented as having the formula:

(Ia)

wherein $R_8$ is hydrogen or carbamoyl.

DETAILED DESCRIPTION OF THE INVENTION

The lower alkyl groups referred to throughout this specification include straight or branched chain hydrocarbon groups containing 1 to 4 carbons, e.g., methyl, ethyl, i-propyl, t-butyl, etc.

The compounds of formula I and their intermediates that are described below that have the 2-amino 4-thiazolyl group as part of their structure are, of course, tautomeric and can also be structurally represented as containing a 2-imino group. Thus, the compounds of formula I can be represented as:

(II)

The intermediates and final products are being structurally represented and named throughout this specification as 2-amino-4-thiazoles though both forms are within the scope of the invention.

The compounds of formula I and the intermediates described below having the oximino substituent $$-\underset{\underset{\underset{|}{O}}{\overset{||}{N}}}{\overset{|}{C}}-$$

can be obtained as the syn or anti isomer or as a mixture of isomers. All of these isomeric forms are within the scope of this invention. However, in general, it is preferred to obtain the final products in the syn form since that isomeric form has the greatest activity.

The symbol $$\overset{(O)_m}{\underset{S}{|}}$$

is being used to represent sulfide alone or bonded to either one or two oxygens. When the sulfide is bonded to only one oxygen the sulfoxides of formula I and in the various intermediates described below can be in either the α- or β- configuration. When the sulfoxide is only in the β-configuration it will be represented as $$\overset{O}{\underset{S}{\overset{\shortparallel}{}}}$$

and when it is only in the α-configuration it will be represented as $$\overset{O}{\underset{S}{\overset{\equiv}{}}}$$

The cephalosporins of formula I can be prepared by various methods. For example, the compounds of formula I wherein $R_4$ is —OCONH$_2$,

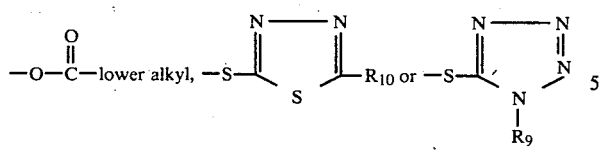

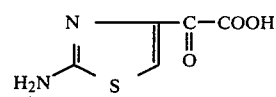

with a compound of the formula

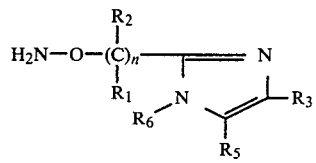

and wherein $R_9$ and $R_{10}$ are as defined above can be obtained by acylating an ester of the formula

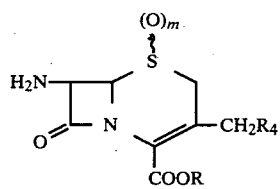

wherein $R_4$, and m are as defined above and R is an ester protecting group such as benzyl, diphenylmethyl, t-butyl, p-methoxybenzyl or trichloroethyl, with a compound of the formula

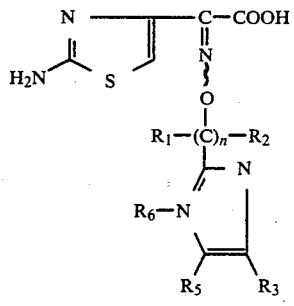

wherein $R_1$, $R_2$, $R_3$, $R_5$, $R_6$ and n are as defined above, to yield an intermediate of the formula

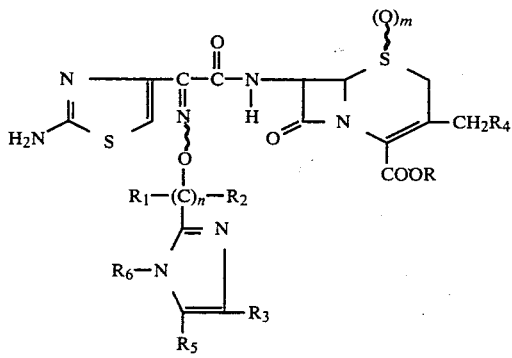

The acylation reaction is carried out in the presence of a coupling agent such as dicyclohexylcarbodiimide.

The intermediate of formula V is then treated to remove the ester protecting group and yield the compounds of formula I in the acid form. Preferably, in the above reactions, R is diphenylmethyl and the intermediate of formula V is treated with trifluoroacetic acid to remove the diphenylmethyl group.

The compounds of formula IV are obtained by reacting 2-amino-4-thiazole glyoxylic acid of the formula The compound of formula VII can be prepared by treating N-hydroxyphthalimide sodium salt with a compound of the formula

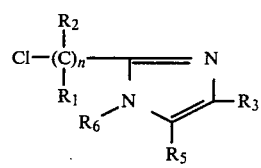

to yield the compound of the formula

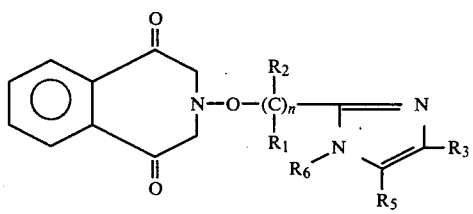

Treatment of IX with hydrochloric acid yields the reactant of formula VII.

The 7-amino cephalosporanic acid ester α- and β-sulfoxides of formula III (m is one) are prepared by converting the 7-amino cephalosporanic acid starting material (m is zero) to the Schiff base ester of the formula

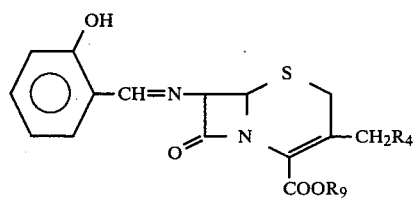

which is then oxidized with a percarboxylic acid such as m-chloroperbenzoic acid to yield a mixture of α- and β-sulfoxide Schiff base cephalosporin esters. The Schiff base sidechain is cleaved by treatment with toluenesulfonic acid and the α- and β-sulfoxide 7-amino cephalosporanic acid esters are separated chromatographically. Further oxidation of the α-sulfoxide yields the corresponding sulfone (m is two) of formula III.

The compounds of formula Ia can be prepared by reacting a compound of formula I wherein R is hydrogen and $R_4$ is

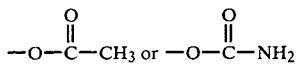

with pyridine or carbamoyl substituted pyridine in a polar solvent such as water and in the presence of a catalyst such as an alkali metal thiocyanate according to the procedures taught in U.S. Pat. No. 3,792,047 and German Offenlegungsschrift No. 2,234,280.

Also, the compounds of formula I wherein $R_4$ is heterothio

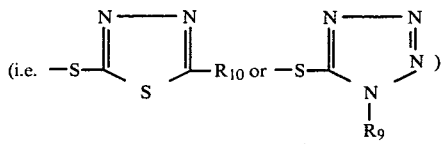

can be prepared by reacting the compound of formula I wherein R is hydrogen and $R_4$ is

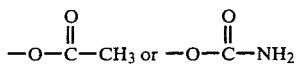

with a mercaptan of the formula hetero-S-H or an alkali metal (preferably sodium) mercaptan salt of the formula hetero-S-alkali metal.

Such methods of introducing a heterothio group in the 3-position are disclosed in various U.S. Pat. Nos. including 3,955,213, 4,066,762, etc.

The β-sulfoxide compounds of formula I (m is one) can also be prepared by the direct oxidation of the corresponding sulfide compound (m is zero). Suitable oxidizing agents are percarboxylic acids such as m-chloroperbenzoic acid, peracetic acid, etc., and this reaction can be performed at from about 0° C. to about 25° C.

Also, the sulfone compounds of formula I (m is two) can be prepared by the direct oxidation of the corresponding α-sulfoxide compound (m is one). Again percarboxylic acids such as m-chloroperbenzoic acid and peracetic acid are the preferred oxidizing agents.

The compounds of formula I wherein R is sodium or potassium are prepared by reacting the corresponding compound of formula I wherein R is hydrogen with the appropriate salt forming ion.

The compounds of formula I wherein R is

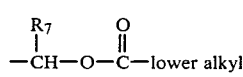

can be obtained by treating the corresponding free acid of formula I with a compound of the formula

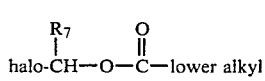

wherein halo is chlorine or bromine in an inert solvent such as dimethylformamide at or below ambient temperature.

Similarly, the compounds of formula I wherein R is

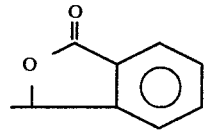

are prepared by treating free acid compound of formula I with a compound of the formula

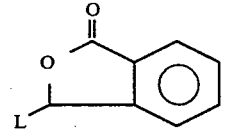

wherein L is hydroxy or Br as taught in U.S. Pat. Nos. 3,860,579, 3,951,954, and 4,072,677.

Preferred compounds of this invention are those of formula I wherein the oximino group is in the syn configuration;

n is one or two m is zero or one provided that when m is one the sulfoxide is in the β-configuration;

R is hydrogen, sodium or potassium;

$R_1$, $R_2$, $R_3$ and $R_5$ are independently selected from hydrogen and methyl;

$R_4$ is

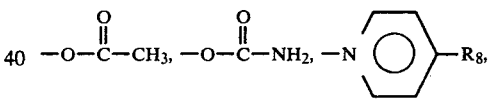

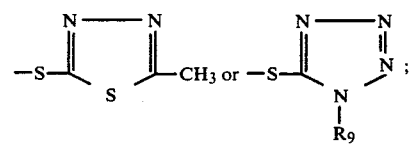

$R_6$ is hydrogen, methyl, benzyl or acetyl;

$R_7$ is hydrogen;

$R_8$ is hydrogen or

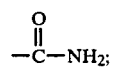

$R_9$ is hydrogen, methyl,

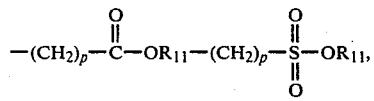

or $-(CH_2)_p-N(CH_3)_2$; $R_{11}$ is hydrogen, sodium or potassium and p is 1 or 2.

Most preferred are the above compounds wherein $R_4$ is

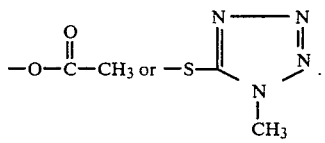

The compounds of formula I wherein R is hydrogen, sodium, potassium or

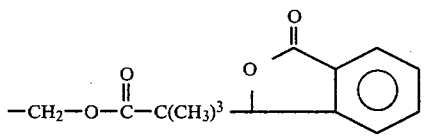

are useful antibacterial agents possessing activity against various gram negative organisms including Klebsiella, Proteus, and Enterobacter species. These compounds are also active against strains of *Escherichia coli, Citrobacter freundii, Salmonella typhimurium*, etc. They may be used as antibacterial agents to combat infections due to organisms such as those named above, and in general may be utilized in a manner similar to other gram-negative antibacterial agents. For example, a compound of formula I or a physiologically acceptable salt thereof may be used in various animal species in an amount of about 1 to 100 mg./kg., daily in parenteral form, in single or two to four divided doses to treat infections of bacterial origin, e.g., 5.0 mg./kg. in mice.

Up to about 600 mg. of an acid compound of formula I or a physiologically acceptable salt or ester thereof may be incorporated in an injectable form prepared according to conventional pharmaceutical practice.

Illustrative process details are in the examples for the various reactions. All temperatures are on the centigrade scale.

EXAMPLE I

[6R-[6α,7β(Z)]]-3-[(Acetyloxy)methyl]-7-[[(2-amino-4-thiazolyl)[(1H-imidazol-2-yl-methoxy)acetyl]amino]-8-oxo-5-thia-1-azabicyclo[4.2.0]oct-2-ene-2-carboxylic acid, sodium salt (a) 2-(1H-Imidazol-1-yl-methoxy)-1H-isoindole-1,3(2H) dione 5.1 g sodium salt of N-hydroxyphthalimide and 1.9 g 2-chloromethyl imidazole hydrochloride (Journal of Chem. Soc. 1965,4577) are stirred at room temperature in dry methanol for 2 hours. The solvent is distilled off in vacuo and the residue treated with aqueous sodium bicarbonate and extracted 3 to 4 times with chloroform. The combined organic layers are dried over sodium sulfate, filtered and evaporated to dryness 1.7 g of 2-(1H-Imidazol-1-yl-methoxy)-1H-isoindole-1,3(2H)dione remains as crystalline solid with a melting point of 158°-160° C.

(b) 2-[(Aminoxy)methyl]-1H-imidazole hydrochloride (1:2)

1.5 g of 2-(1H-imidazol-1-yl-methoxy)-1H-isoindole-1,3(2H) dione is refluxed with stirring for 4 hours in 20 ml of 17.5% HCl aqueous. The mixture is cooled to room temperature and the precipitated phthalic acid is filtered off. The mother liquor is evaporated to dryness. 0.8 g of 2-[(aminoxy)methyl]-1H-imidazole hydrochloride (1:2) remains with a melting point of 182°-183° C.

(c) 2-Amino-α-[(1H-imidazole-2-yl-methoxy)imino]-4-thiazole acetic acid, hydrochloride (1:2) (Z)

2 g of 2-[(aminoxy)methyl]-1H-imidazolehydrochloride (1:2) from example 1(b) and 2.24 g 2-amino-thiazol-4-glyoxylic acid are suspended with stirring in 50 ml H₂O. The pH is adjusted with potassium carbonate to 6 and stirring is continued for 12 hours. The pH is then adjusted to 6.4 with hydrochloric acid. After 2 hours 0.8 of crystalline 2-amino-α-[(1H-imidazol-2-yl-methoxy)imino]-4-thiazole acetic acid hydrochloride (1:2) is filtered off with a melting point of 158°-160° C. (dec.).

(d) [6R-[6α,7β(Z)]]-3-[(Acetyloxy)methyl]-7-[[(2-amino-4-thiazolyl) [(1H-imidazol-2-yl-methoxy)-imino]acetyl]amino]-8-oxo-5-thia-1-azabicyclo[4.2.0]oct-2-ene-2-carboxylic acid, diphenylmethyl ester.

1.2 g 2-Amino-α-[(1H-imidazol-2-yl-methoxy)imino]-4-thiazole acetic acid hydrochloride (1:2) of example 1 (c), 1.84 g 7ACA-benzhydryl ester and 0.54 g Hydroxybenzotriazole are dissolved in 50 ml dimethylformamide (DMF). At 0° C. 1.1 g of dicyclohexylcarbodiimide in 20 ml of acetonitrile is added to the DMF solution and stirred for 24 hours at 0° C. After this time the solvent is removed in vacuo and the residue dissolved in acetone and filtered. The mother liquor is evaporated to dryness and the oily residue poured into 0° C. aqueous sodium bicarbonate. The crystalline precipitate is filtered off, and purified by column chromatography using SiO₂ and ethyl acetate as eluant to yield 1.5 g [6R-[6α,7β(Z)]]-3-[(Acetyloxy)methyl]-7-[[(2-amino-4-thiazolyl) [(1H-imidazol-2-yl-methoxy)-imino]acetyl]-amino]-8-oxo-5-thia-1azabicyclo[4.2.0]oct-2-ene-2-carboxylic acid, diphenylmethyl ester with a melting point of 115° C. (dec.).

(e) [6R-[6α,7β(z)]]-3-[(Acetyloxy)methyl]-7-[[(2-amino-4-thiazolyl)](1H-imidazol-2-yl-methoxy)imino]acetyl]-amino]-8-oxo-5-thia-1-azabicyclo[4.2.0]oct-2-ene-2-carboxylic acid, trifluoroacetate salt 920 mg of [6R-[6α,7β(Z)]]-3-[(Acetyloxy)methyl]-7-[[(2-amino-4-thiazolyl)[(1H-imidazol-2-yl-methoxy)-imino]acetyl]amino]-8-oxo-5-thia-1-azabicyclo[4.2.-0]oct-2-ene-2-carboxylic acid, diphenylmethyl ester is suspended in 2.5 ml anisole with stirring at 0° C. 5 ml trifluoroacetic acid are added and the mixture is stirred for an additional hour at 0° C. After this time the solution is poured into 100 ml of a 1:1 mixture of ether/petrol ether. The precipitated acid is filtered off, washed with ether and dried to yield 850 mg of [6R-[6α,7β(Z)]]-3-[(Acetyloxy)methyl]-7-[[(2-amino-4-thiazolyl)[(1H-imidazol-2-yl-methoxy)imino]acetyl]-amino]-8-oxo-5-thia-1-azabicyclo[4.2.0]oct-2-ene-2-carboxylic acid trifluoroacetate salt.

(f) [6R-[6α,7β(Z)]]-3-[(Acetyloxy)methyl]-7-[[(2-amino-4-thiazolyl)[(1H-imidazol-2-yl-methoxy)imino]acetyl]-amino]-8-oxo-5-thia-1-azabicylo[4.2.0]oct-2-ene-2-carboxylic acid, sodium salt 850 mg of [6R-[6α,7β(Z)]]-3-[(Acetyloxy)methyl]-7-[[(2-amino-4-thiazolyl)[(1H-imidazol-2-yl-methoxy)-imino]acetyl]amino]-8-oxo-5-thia-1-azabicyclo[4.2.0]-oct-2-ene-2-carboxylic acid, trifluoroacetate salt is dissolved in 15 ml of dry acetone/methanol (1:1) and treated at 0° C. with 765 mg of sodium ethylhexanoate in 5 ml butanol. After 10 minutes stirring the mixture is poured into 100 ml of ether and 630 mg of precipitated [6R-[6α,7β(Z)]]-3-[(acetyloxy)methyl]-7-[[(2-amino-4-thiazolyl)[(1H-imidazol-2-yl-methoxy)imino]acetyl]-amino]-8-oxo-5-thia-1-azabicyclo[4.2.0]oct-2-ene-2-carboxylic acid, sodium salt is filtered off having a melting point of 163°–165° C.

EXAMPLE 2

[5S[5α,6β,7α(Z)]]-3[(Acetyloxy)methyl]-7-[[(2-amino-4-thiazolyl)[(1H-imidazol-2-yl-methoxy)imino]acetyl]-amino]-8-oxo-5-thia-1-azabicyclo[4.2.0]oct-2-ene-2-carboxylic acid, 5-oxide sodium salt (a)

[5S[5α,6β,7α(Z)]]-3[(Acetyloxy)methyl]-7-[[(2-amino-4-thiazolyl)[(1H-imidazol-2-yl-methoxy)imino]acetyl]-amino]-8-oxo-5-thia-1-azabicyclo[4.2.0]oct-2-ene-2-carboxylic acid, 5-oxide benzhydryl ester 2 g of 2-amino-α-[(1H-imidazol-2-yl-methoxy)imino]-4-thiazole acetic acid hydrochloride (1:2) of example 1c, 2.95 g of 7ACA-benzhydrylester-β-sulfoxide and 1.2 g hydroxybenzotriazole are dissolved in 80 ml dimethylformamide cooled to 0° C. and 1.8 g dicyclohexylcarbodiimide is added. The solution is stirred at 0° C. over night. The solvent is removed in vacuo and the oily residue stirred at 0° C. with aqueous sodium bicarbonate solution. The precipitated compound is filtered off, and purified by column chromatography using SiO$_2$ and acetone as eluent to yield 2.2 g of [5S[5α,6β,7α(Z)]]-3[(acetyloxy)methyl]-7-[[(2-amino-4-thiazolyl)[(1H-imidazol-2-yl-methoxy)imino]-acetyl]-amino]-8-oxo-5-thia-1-azabicyclo[4.2.0]oct-2-ene-2-carboxylic acid, 5-oxide benzhydryl ester.

(b)

[5S[5α,6β,7α(Z)]]-3[(Acetyloxy)methyl]-7-[[(2-amino-4-thiazolyl)[(1H-imidazol-2-yl-methoxy)imino]acetyl]-amino]-8-oxo-5-thia-1-azabicyclo[4.2.0]oct-2-ene-2-carboxylic acid, 5-oxide trifluoroacetate A slurry of 2 g of [5S[5α,6β,7α(Z)]]-3-[(acetyloxy)methyl]-7-[[(2-amino-4-thiazolyl)[(1H-imidazol-2-yl-methoxy)imino]acetyl]-amino]-8-oxo-5-thia-1-azabicyclo-[4.2.0]oct-2-ene-2-carboxylic acid, 5-oxide benzhydryl ester and 6 g anisole are stirred at 0° C., while 8 ml of trifluoroacetic acid is added. Stirring is continued for 45 minutes and the solution is now poured into 200 ml of ether. The precipitate is filtered and washed with ether to yield 1.8 g of [5S[5α,6β,7α(Z)]]-3-[(acetyloxy)methyl]-7-[[(2-amino-4-thiazolyl)[(1H-imidazol-2-yl-methoxy)-imino]acetyl]-amino]-8-oxo-5-thia-1-azabicyclo[4.2.0]oct-2-ene-2-carboxylic acid, 5-oxide trifluoroacetate.

(c)

[5S[5α,6β,7α(Z)]]-3-[(Acetyloxy)methyl]-7-[[(2-amino-4-thiazolyl)[(1H-imidazol-2-yl-methoxy)imino]acetyl]-amino]-8-oxo-5-thia-1-azabicyclo[4.2.0]oct-2-ene-2-carboxylic acid, 5-oxide sodium salt 1.9 g of [5S[5α,6β,7α(Z)]]-3-[(acetyloxy)methyl]-7-[[(2-amino-4-thiazolyl)[(1H-imidazol-2-yl-methoxy)imino]acetyl]-amino]-8-oxo-5-thia-1-azabicyclo[4.2.0]oct-2-ene-2-carboxylic acid trifluoroacetate of Example 2(b) are treated in 5 ml dimethylformamide/methanol (1:1) for 5 minutes with stirring. 200 ml of ether are added and the precipitated sodium salt is filtered off, yielding 1.1 g of [5S[5α,6β,7α(Z)]]-3-[(acetyloxy)methyl]-7-[[(2-amino-4-thiazolyl)[(1H-imidazol-2-yl-methoxy)imino]-acetyl]-amino]-8-oxo-5-thia-1-azabicyclo[4.2.0]oct-2-ene-2-carboxylic acid, 5-oxide sodium salt having a melting point of 140°–145° C. (dec.).

EXAMPLE 3

[6R-[6α,7β(Z)]]-7-[[(2-Amino-4-thiazolyl)[(1H-imidazol-2-yl-methoxy)imino]acetyl]-amino]-3-[[(1-methyl-1H-tetrazol-5-yl)thio]methyl]-8-oxo-5-thia-1-azabicyclo-[4.2.0]oct-2-ene-2-carboxylic acid, sodium salt When 2-Amino-α-[(1H-imidazol-2-yl-methoxy)imino]-4-thiazole acetic acid hydrochloride (1:2) of example 1 (c) is reacted with 3-(1-methyl-1H-tetrazolyl)-7ACA-benzhydryl ester according to the procedure given in Example 1(d), [6R-[6α,7β(Z)]]-7-[[-(Amino-4-thiazolyl)-[(1H-imidazol-2-yl-methoxy)imino]acetyl]-amino]-3[[(1-methyl-1H-tetrazol-5-yl)thio]methyl]-8-oxo-5-thia-1-azabicyclo[4.2.0]oct-2-ene-2-carboxylic acid, diphenylmethyl ester is obtained. This compound is then processed as described in Example 1(e) and 1(f), i.e. cleavage of the benzhydryl moiety by treatment with trifluoroacetic acid and subsequent formation of the sodium salt. By this method [6R-[6α,7β(Z)]]-7-[[(2-amino-4-thiazolyl)-[(1H-imidazol-2-yl-methoxy)imino]acetyl]-amino]-3-[[(1-methyl-1H-tetrazolyl-5-yl)thio]methyl]-8-oxo-5-thia-1-azabicyclo[4.2.0]oct-2-ene-2-carboxylic acid, sodium salt is obtained; having a melting point of 198°–200° C. (dec.).

EXAMPLE 4

[5S-[5α,6β,7α(Z)]]-3-[(Acetyloxy)methyl]-7-[[(2-amino-4-thiazolyl)[(1H-imidazol-2-yl-methoxy)imino]acetyl]amino]-8-oxo-5-thia-1-azabicyclo[4.2.0]oct-2-ene-2-carboxylic acid, 5,5 dioxide sodium salt (a)

[5S-[5α,6β,7α]]-3-[(Acetyloxy)methyl]-7-amino-8-oxo-5-thia-1-azabicyclo[4.2.0]oct-2-ene-2-carboxylic acid, 5-oxide, diphenylmethyl ester (i.e., β-sulfoxide) and [5R-[5α,6α,7β]]-3-[(Acetyloxy)methyl]-7-amino-8-oxo-5-thia-1-azabicyclo[4.2.0]oct-2-ene-2-carboxylic acid, 5-oxide, diphenylmethyl ester (i.e., α-sulfoxide)

A slurry of 50 g of 7-aminocephalosporanic acid (7-ACA) in 1 liter of water is stirred magnetically while t-octyl amine is added dropwise, thereby maintaining the pH between 7 and 8. After one hour the undissolved solid is filtered (celite) and the filtrate is treated with a solution prepared by adjusting a mixture of 10 ml of 5-octylamine and 20 ml of water to pH 8.0 with 6 N hydrochloric acid. The resulting solution is then treated with 10 ml of salicylaldehyde. After 2 minutes a solid forms and after 5 minutes an additional 10 ml of salicylaldehyde is added. The slurry is stirred for an additional 10 minutes, cooled to 0° to 4.5 hours and filtered. The filter cake is slurried twice with 300 ml of cold water and filtered. The wet cake is dried at 60° in vacuo over large amounts of P$_2$O$_5$ to give 66 g of tan solid 7-salicylaldiminocephalosporanic acid, t-octyl amine salt.

A slurry of 25.25 g (0.05 mole) of the above t-octyl amine salt (powdered with a mortar and pestle) in 250 ml of dry acetonitrile is treated with 9.5 g (0.05 mole) of p-toluenesulfonic acid monohydrate. After 10 minutes, a solution of 9.7 g (0.05 mole) of diphenyldiazomethane in 50 ml of acetonitrile is added over the course of 15 minutes. After one hour, the slurry is filtered, the solid is washed with acetonitrile, and the combined filtrate and washings are evaporated in vacuo. The resulting oil is chromatographed on a 300 g silica gel column eluted with methylene chloride. Fractions (500 ml) 2–3 contain 7.5 g of the desired diphenylmethyl ester product plus some higher $R_f$ impurity (monitored by silica gel TLC with 3:1 chloroform-ethyl acetate development):fractions 4–11 contain 12.3 g of pure 7-salicyclaldiminocephalosporanic acid, diphenylmethyl ester; NMR (CDCl$_3$)δ1.97 (s, 3H, CH$_3$CO); 3.23 and 3.60 (AB q, J=19 Hz, 2H, c-2); 4.67 and 5.01 (AB q, J=14 Hz, 2H, C-3'); 4.99 (d, J=5 Hz, 1H, c-6); 5.20 (broadened d, J=5 Hz, 1H, C-7); 6.62–7.60 (m, about 15H); 9.07 (broad s, 1H, —CH=N—).

A solution of 12.3 g (0.023 mole) of the above diphenylmethyl ester product in 125 ml of methylene chloride is cooled to 0° and a solution of 4.6 g (0.023 mole) of 85% m-chloroperbenzoic acid in 70 ml of methylene chloride is added over the course of 15 minutes. After one hour, the slurry is washed with a mixture of 100 ml of 5% sodium bicarbonate and 50 ml of 6% sodium sulfite solution. The organic layer is dried and evaporated in vacuo. The resulting oil crystallizes from 70 ml of ethyl acetate giving 8.7 g of a mixture of α- and β-sulfoxides. A second crop of 1.5 g of a mixture of α- and β-sulfoxides is also obtained. The major (α-) isomer has a lower field acetate methyl (2.02 ppm) and C-2 quartet (3.57 and 4.10 ppm) when compared to those of the minor (β) isomer (1.97, 3.26 and 3.94 ppm, respectively).

A slurry of 10 g (0.018 mole) of the above 7-salicyladiminocephalosporanic acid, diphenylmethyl ester α- and β-sulfoxide mixture in 100 ml of ethyl acetate is treated with 3.42 g (0.018 mole) of p-toluenesulfonic acid monohydrate. After 5.5 hours, 300 ml of ether is added and the gummy solid is triturated, filtered, and washed twice with ether. The moist solid is dissolved in 200 ml of ethyl acetate and the solution is washed with 100 ml of 5% sodium bicarbonate solution, dried, and evaporated to give 8.0 g of residue. Chromatography on a 300 g silica gel column eluted with 3:1 chloroformethyl acetate gives (500 ml fractions): fraction 3, 1.0 g of recovered 7-salicylaldimino-cephalosporanic acid, diphenylmethyl ester; fractions 6–16, 4.5 g of [5R-[5α,6α,7β]]-3-[(acetyloxy)methyl]-7-amino-8-oxo-5-thia-1-azabicyclo[4.2.0]oct-2-ene-2-carboxylic acid, 5-oxide, diphenylmethyl ester (i.e., α-sulfoxide isomer):NMR (CDCl$_3$)δ2.00 (CH$_3$COO—); 3.43 and 4.06 ppm (AB q, C-2); fractions 22–30 (eluant is changed to ethyl acetate after fraction 16) 1.5 g of [5S-[5α,6β,7α]]-3-[(acetyloxy)methyl]-7-amino-8-oxo-5-thia-1-azabicyclo[4.2.0]oct-2-ene-2-carboxylic acid, 5-oxide, diphenylmethyl ester (i.e., β-sulfoxide isomer):NMR (CDCl$_3$)δ2.10 (CH$_3$COO—); 2.97 and 3.54 ppm (AB q, C-2).

(b)
[6R-[6α,7β]]-3-[(Acetyloxy)methyl]-7-amino-8-oxo-5-thia-1-azabicyclo[4.2.0]oct-2-ene-2-carboxylic acid, 5,-5-dioxide, diphenylmethyl ester

[5R-[5α,6α,7β]]-3-[(Acetyloxy)methyl]-7-amino-8-oxo-5-thia-1-azabicyclo[4.2.0]oct-2-ene-2-carboxylic acid, 5-oxide, diphenylmethyl ester from Example 4(a) is added to methylene chloride and cooled to 0°. An equimolar amount of m-chloroperbenzoic acid in methylene chloride is added. After the reaction is completed, the slurry is treated with 5% sodium bicarbonate and 5% sodium sulfite. The organic layer is dried and evaporated in vacuo. Preparative thin layer chromatography of the residue yields [6R-[6α,7β]]-3-[(acetyloxy)methyl]-7-amino-8-oxo-5 thia-1-azabicyclo[4.2.0]oct-2-ene-2-carboxylic acid, 5,5-dioxide, diphenylmethyl ester.

(c)
[5S-[5α,6β,7α(Z)]]-3-[(Acetyloxy)methyl]-7-[[(2-amino-4-thiazolyl)[(1H-imidazol-2-yl-methoxy)imino]acetyl]-amino]-8-oxo-5-thia-1-azabicyclo[4.2.-0]oct-2-ene-2-carboxylic acid, 5,5-dioxide, diphenylmethyl ester Following the procedure of Example 1(d) but substituting [5S-[5α,6β,7α]]-3-[(acetyloxy)methyl]-7-amino-8-oxo-5-thia-1-azabicyclo[4.2.0]oct-2-ene-2-carboxylic acid, 5,5-dioxide, diphenylmethyl ester for 7 ACA-diphenylmethyl ester then [5S-[5α,6β,7α(Z)]]-3-[(acetyloxy)-methyl]-7-[[(2-amino-4-thiazolyl[(1H-imidazol-2-yl-methoxy)imino]acetyl]amino]-8-oxo-5-thia-1-azabicyclo[4.2.0]-oct-2-ene-2-carboxylic acid 5,5 dioxide, diphenylmethyl ester is formed.

(d)
[5S-(5α,6β,7α)]-3-[(Acetyloxy)methyl]-7-[[(2-amino-4-thiazolyl)[(1H-imidazol-2-yl-methoxy)imino]acetyl]amino]-8-oxo-5-thia-1-azabicyclo[4.2.0]oct-2-ene-2-carboxylic acid 5,5 dioxide trifluoroacetate salt Following the procedure of Example 1(e) but substituting [5S-[5α,6β,7α(Z)]]-3-[(acetyloxy)methyl]-7-[[-(2-amino-4-thiazolyl)[(1H-imidazol-2-yl-methoxy)imino]acetyl]amino]-8-oxo-5-thia-1-azabicyclo[4.2.0]oct-2-ene-2-carboxylic acid 5,5-dioxide diphenylmethyl ester for [6R-[6α,7β(Z)]]-3-[(acetyloxy)methyl]-7-[[(2-amino-4-thiazolyl)[(1H-imidazol-2-yl-methoxy)imino]acetyl]amino]-8-oxo-5-thia-1-azabicyclo[4.2.-0]oct-2-ene-2-carboxylic acid, diphenylmethyl ester then [5S-(5α,6β,7α)]-3-[(acetyloxy)methyl]-7-[[(2-amino-4-thiazolyl)[(1H-imidazol-2-yl-methoxy)imino]acetyl]amino]-8-oxo-5-thia-1-azabicyclo-[4.2.0]oct-2-ene-2-carboxylic acid 5,5 dioxide trifluoroacetate salt is formed.

(e)
[5S-[5α,6β,7α(Z)]]-3-[(Acetyloxy)methyl]-7-[[(2-amino-4-thiazolyl)[(1H-imidazol-2-yl-methoxy)imino]acetyl]amino]-8-oxo-5-thia-1-azabicyclo[4.2.-0]oct-2-ene-2-carboxylic acid, 5,5 dioxide, sodium salt Following the procedure of Example 1(f) but substituting [5S-(5α,6β,7α)]-3-[(acetyloxy)methyl]-7-[[(2-amino-4-thiazolyl)[(1H-imidazol-2-yl-methoxy)imino]acetyl]amino]-8-oxo-5-thia-1-azabicyclo[4.2.0]oct-2-ene-2-carboxylic acid 5,5 dioxide trifluoroacetate salt for [6R-[6α,7β(Z)]]-3-[(acetyloxy)methyl]-7-[[(2-amino-4-thiazolyl)[(1H-imidazol-2-yl-methoxy)imino]acetyl]amino]-8-oxo-5-thia-1-azabicyclo[4.2.0]oct-2-ene-2-carboxylic acid, trifluoroacetate salt to form [5S-[5α,6β,7β(Z)]]-3-[(acetyloxy)methyl]-7-[[(2-amino-4-thiazolyl)[(1H-imidazol-2-yl-methoxy)imino]acetyl]amino]-8-oxo-5-thia-1-azabicyclo[4.2.0]oct-2-ene-2-carboxylic acid, 5,5 dioxide, sodium salt.

EXAMPLE 5

[5R-[5α,6α,7β]]-3-[(Acetyloxy)methyl]-7-[[(2-amino-4-thiazolyl)[(1H-imidazol-2-yl-methoxy)imino]acetyl]amino]-8-oxo-5-thia-1-azabicyclo[4.2.0]oct-2-ene-2-carboxylic acid, 5-oxide, sodium salt (i.e. α-sulfoxide)

(a)

[5R-[5α,6α,7β]]-3-[(Acetyloxy)methyl]-7-[[(2-amino-4-thiazolyl)[(1H-imidazol-2-yl-methoxy)imino]acetyl]amino]-8-oxo-5-thia-1-azabicyclo[4.2.0]oct-2-ene-2-carboxylic acid 5-oxide, diphenylmethyl ester Following the procedure of Example 1(d) but substituting [5R-[5α,6α,7β]]-3-[(acetyloxy)methyl]-7-amino-8-oxo-5-thia-1-azabicyclo[4.2.0]oct-2-ene-2-carboxylic acid, 5-oxide, diphenylmethyl ester (i.e. α-sulfoxide) (made as in Example 4(a) for 7 ACA-diphenylmethyl ester, then [5R-[5α,6α,7β]]-3-[(acetyloxy)methyl]-7--[[(2-amino-4-thiazolyl[(1H-imidazol-2-yl-methoxy)imino]-acetyl]amino]-8-oxo-5-thia-1-azabicyclo[4.2.-0]oct-2-ene-2-carboxylic acid 5-oxide, diphenylmethyl ester is formed.

(b)

[5R-[5α,6α,7β]]-3-[(Acetyloxy)methyl]-7-[[(2-amino-4-thiazolyl)[(1H-imidazol-2-yl-methoxy)imino]acetyl]amino]-8-oxo-5-thia-1-azabicyclo[4.2.0]oct-2-ene-2-carboxylic acid, 5-oxide, trifluoroacetate Following the procedure of Example 1(e) but substituting [5R-[5α,6α,7β]]-3-[(Acetyloxy)methyl]-7-[[(2-amino-4-thiazolyl[(1H-imidazol-2-yl-methoxy)imino]acetyl]-amino]-8-oxo-5-thia-1-azabicyclo[4.2.-0]oct-2-ene-2-carboxylic acid 5-oxide, diphenylmethyl ester in place of [6R-[6α,7β(Z)]]-3-[(acetyloxy)methyl]-7-[[(2-amino-4-thiazolyl)[(1H-imidazol-2-yl-methoxy)imino]acetyl]amino]-8-oxo-5-thia-1-azabicyclo[4.2.0]oct-2-ene-2-carboxylic acid diphenylmethyl ester then [5R-[5α,6α,7β]]-3-[(acetyloxy)methyl]-7-[[-(2-amino-4-thiazolyl)[(1H-imidazol-2-yl-methoxy)imino]acetyl]amino]-8-oxo-5-thia-1-azabicyclo-[4.2.0]oct-2-ene-2-carboxylic acid, 5-oxide, trifluoroacetate is formed.

(c)

[5R-[5α,6α,7β]]-3[[(Acetyloxy)methyl]-7-[[(2-amino-4-thiazolyl)[(1H-imidazol-2-yl-methoxy)imino]acetyl]amino]-8-oxo-5-thia-1-azabicyclo[4.2.0]oct-2-ene-2-carboxylic acid, 5-oxide, sodium salt (i.e. α-sulfoxide)

Following the procedure of Example 1(f) but substituting [5R-[5α,6α,7β]]-3-[(acetyloxy)methyl]-7-[[(2--amino-4-thiazolyl)[(1H-imidazol-2-yl-methoxy)imino]-acetyl]amino]-8-oxo-5-thia-1-azabicyclo[4.2.0]oct-2-ene-2-carboxylic acid, 5-oxide, trifluoroacetate in place of [6R-[6α,7β(Z)]]-3-[(acetyloxy)methyl]-7-[[(2-amino-4-thiazolyl)](1H-imidazol-2-yl-methoxy)imino]acetyl]amino]-8-oxo-5-thia-1-azabicyclo[4.2.-0]oct-2-ene-2-carboxylic acid, trifluoroacetate salt then [5R-[5α,6α,7β]]-3-[(-acetyloxy)methyl]-7-[[(2-amino-4-thiazolyl)[(1H-imidazol-2-yl-methoxy)imino]acetyl]amino]-8-oxo-5-thia-1-azabicyclo[4.2.0]oct-2-ene-2-carboxylic acid, 5-oxide, sodium salt (i.e. α-sulfoxide) is formed.

EXAMPLES 6–31

Following the procedure of Examples 1 to 5 but employing the ester shown in Col. I and the acid shown in Col. II one obtains the ester shown in Col. III. Removal of the ester protecting group yields the acid product shown in Col. IV.

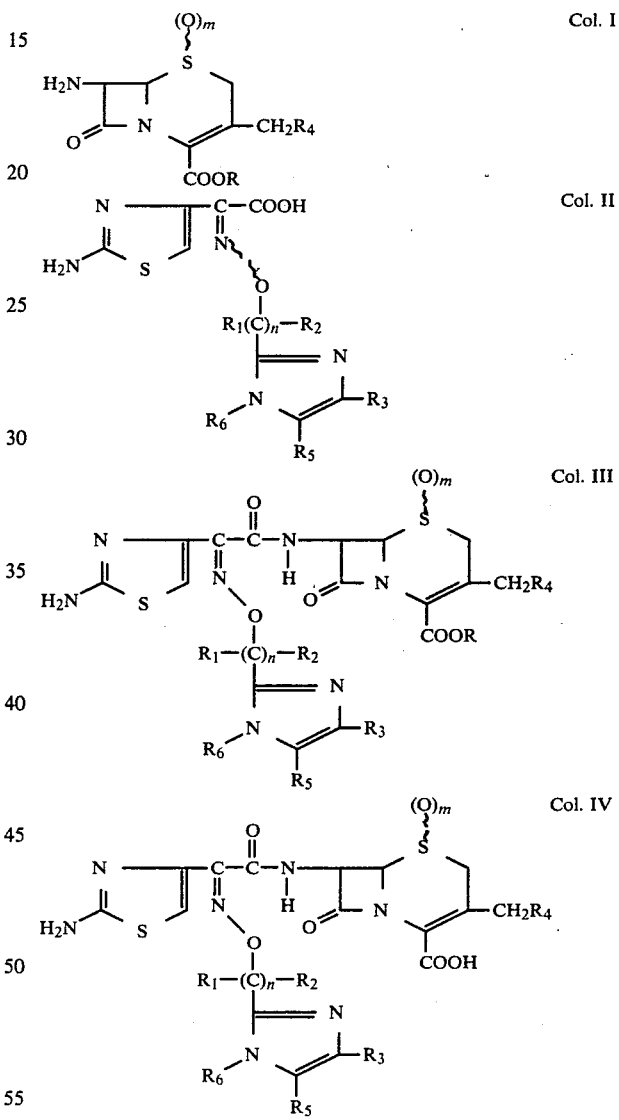

| Example | R4 | R | R1 | R2 | R3 | R5 | R6 | m | n |
|---|---|---|---|---|---|---|---|---|---|
| 6 | —O—C(=O)—CH3 | —CH(—C6H5)2 | —H | —H | —H | —H | —CH3 | one | two |
| 7 | —O—C(=O)—CH3 | —C(CH3)3 | —H | —H | —CH3 | —H | —CH3 | zero | one |
| 8 | —O—C(=O)—CH3 | —CH2—C6H4—OCH3 | —CH3 | —CH3 | —CH3 | —H | —CH3 | zero | one |

-continued

| Example | R₄ | R | R₁ | R₂ | R₃ | R₅ | R₆ | m | n |
|---|---|---|---|---|---|---|---|---|---|
| 9 | −O−C(=O)−CH₃ | −CH(−C₆H₅)₂ | −H | −H | −CH₃ | −H | −CH₃ | zero | one |
| 10 | −O−C(=O)−CH₃ | −CH(−C₆H₅)₂ | −H | −H | −CH₃ | −H | −H | two | one |
| 11 | −O−C(=O)−CH₃ | −CH(−C₆H₅)₂ | −CH₃ | −CH₃ | −CH₃ | −H | −H | zero | one |
| 12 | −O−C(=O)−C₂H₅ | −CH(−C₆H₅)₂ | −H | −H | −CH₃ | −H | −CH₃ | zero | one |
| 13 | −H | −CH(−C₆H₅)₂ | −H | −H | −CH₃ | −H | −CH₃ | zero | one |
| 14 | −O−C(=O)−C₂H₅ | −CH(−C₆H₅)₂ | −CH₃ | −H | −CH₃ | −H | −H | zero | one |
| 15 | −O−C(=O)−NH₂ | −CH(−C₆H₅)₂ |  |  | −H | −H | −CH₃ | zero | zero |
| 16 | −O−C(=O)−NH₂ | −CH(−C₆H₅)₂ |  |  | −H | −H | −CH₃ | one | zero |
| 17 | −O−C(=O)−NH₂ | −CH(−C₆H₅)₂ | −H | −H | −H | −H | −CH₃ | one | one |
| 18 | −O−C(=O)−NH₂ | −CH(−C₆H₅)₂ | −H | −H | −H | −H | −CH₃ | two | one |
| 19 | −O−C(=O)−NH₂ | −CH(−C₆H₅)₂ | −CH₃ | −CH₃ | −H | −H | −CH₃ | zero | one |
| 20 | −S−(5-methyl-1,3,4-thiadiazol-2-yl) | −CH(−C₆H₅)₂ | −H | −H | −H | −H | −CH₃ | zero | one |
| 21 | −S−(5-methyl-1,3,4-thiadiazol-2-yl) | −CH(−C₆H₅)₂ | −CH₃ | −H | −H | −H | −CH₃ | zero | one |
| 22 | −S−(5-methyl-1,3,4-thiadiazol-2-yl) | −CH(−C₆H₅)₂ | −H | −H | −H | −H | −H | zero | one |
| 23 | −S−(5-methyl-1,3,4-thiadiazol-2-yl) | −CH(−C₆H₅)₂ | −H | −H | −H | −H | −H | one | one |
| 24 | −S−(1-methyl-1H-tetrazol-5-yl) | −CH(−C₆H₅)₂ | −H | −H | −H | −H | −CH₃ | zero | one |
| 25 | −S−(1-methyl-1H-tetrazol-5-yl) | −CH(−C₆H₅)₂ | −H | −H | −H | −H | −CH₃ | one | one |
| 26 | −S−(1-methyl-1H-tetrazol-5-yl) | −CH(−C₆H₅)₂ | −CH₃ | −CH₃ | −H | −H | −CH₃ | one | one |
| 27 | −S−(1-methyl-1H-tetrazol-5-yl) | −CH(−C₆H₅)₂ | −CH₃ | −CH₃ | −H | −H | −CH₃ | zero | one |
| 28 | −S−(1-CH₂SO₃H-1H-tetrazol-5-yl) | −CH(−C₆H₅)₂ | −H | −H | −H | −H | −CH₃ | zero | one |

-continued

| Example | R₄ | R | R₁ | R₂ | R₃ | R₅ | R₆ | m | n |
|---|---|---|---|---|---|---|---|---|---|
| 29 | -S-[triazole with N-CH₂COOH] | -CH(-C₆H₅)₂ | -H | -H | -H | -H | -CH₃ | zero | one |
| 30 | -S-[triazole with N-H] | -CH₂-C₆H₅ | -H | -H | -H | -H | -CH₃ | one | one |
| 31 | [triazole with N-(CH₂)₂N(CH₃)₂] | -CH(-C₆H₅)₂ | -H | -H | -H | -H | -CH₃ | zero | one |

The acid products of Examples 6 to 31 can be converted to the sodium or potassium according to known procedures.

The products of Examples 6 to 31 are obtained as the syn or anti isomer depending upon the configuration of the acid shown in Col. II. Also, when $R_1$ and $R_2$ are not the same, the products are obtained in the D-, L- or D,L-form depending upon the optical activity of the acid shown in Col. II.

EXAMPLE 32

[6R-[6α,7β(Z)]]-3-[[4-(Aminocarbonyl)pyridino]methyl]-7-[[(2-amino-4-thiazolyl) [(1H-imidazol-2-yl-methoxy)imino]-acetyl]amino]-8-oxo-5-thia-1-azabicyclo[4.2.0]oct-2-ene-2-carboxylic acid, (syn isomer)

A mixture of 0.005 mole of the sodium salt product of Example 1, 0.0075 mole of 4-pyridinecarboximide, 12 g of potassium thiocyanate, and 7.5 ml of water are heated at 50° for 24 hours. The resulting solution is passed through a chromatography column filled with the ion exchange Amberlite XAD-2. The column is washed with water and the titled compound is eluted with a mixture of water:methanol (8:2). The methanol is evaporated from the eluate and the aqueous solution is lyophilized. The amorphous residue is triturated with ether and filtered under suction to yield [6R-[6α,7β(Z)]]-3-[[4-(aminocarbonyl)pyridino]methyl]-7-[[(2-amino-4-thiazolyl) [(1H-imidazol-2-yl-methoxy)imino]acetyl]amino]-8-oxo-5-thia-1-azabicyclo[4.2.0]oct-2-ene-2-carboxylic acid.

EXAMPLES 33–40

Following the procedure of Example 32 but employing the cephalosporanic acid sodium salt shown in Col. I and the pyridine compound shown in Col. II, one obtains the product shown in Col. III.

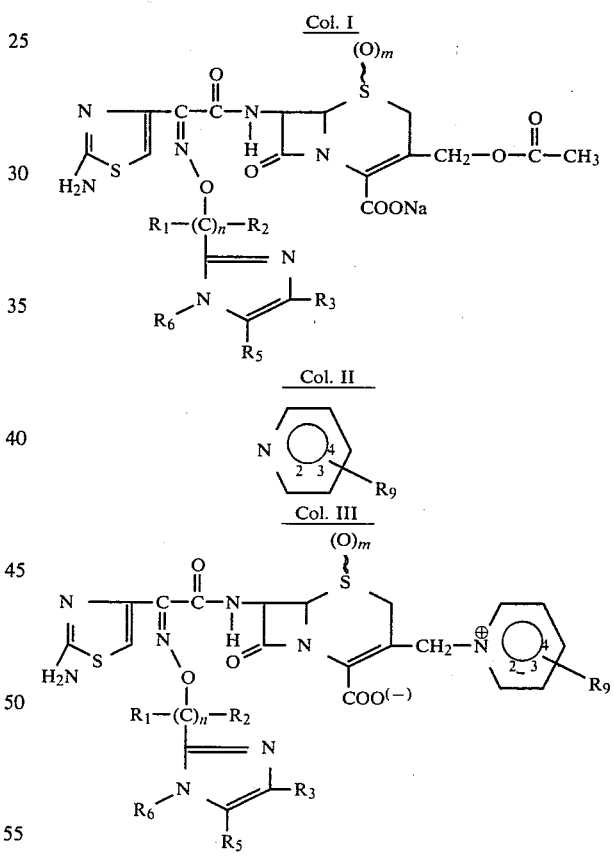

| Example | R₁ | R₂ | R₃ | R₅ | R₆ | m | n | R₉ |
|---|---|---|---|---|---|---|---|---|
| 33 | | | -H | -H | -CH₃ | one | zero | -CONH₂ (4) |
| 34 | | | -H | -H | -CH₃ | two | zero | -CONH₂ (3) |
| 35 | -H | -H | -H | -H | -CH₃ | zero | one | -H |
| 36 | | | -H | -H | -H | zero | zero | -H |
| 37 | | | -H | -H | -H | one | zero | -CONH₂ (4) |

-continued

| Example | R₁ | R₂ | R₃ | R₅ | R₆ | m | n | R₉ |
|---|---|---|---|---|---|---|---|---|
| 38 | —CH₃ | —CH₃ | —H | —H | —H | zero | one | $\overset{O}{\underset{\|}{-C}}NH_2$ (2) |
| 39 |  |  | —H | —H | —H | zero | zero | —H |
| 40 | —H | —H | —H | —CH₃ | —H | zero | one | $\overset{O}{\underset{\|}{-C}}NH_2$ (4) |

The products of Examples 33 to 40 are obtained in the syn or anti configuration depending upon the configuration of the 3-acetoxymethyl starting material shown in Col. I. Similarly, when m is one the compounds are obtained as the α- or β-sulfoxide depending upon the orientation of the 3-acetoxymethyl sulfoxide starting material. Also, when R₁ and R₂ are not the same, the products are obtained in the D-, L- or D,L-isomeric form depending upon the optical activity of the starting material shown in Col. I.

EXAMPLE 41

[6R-[6α,7β(Z)]]-7-[[(2-Amino-4-thiazolyl)[(1H-imidazol-2-yl-methoxy)imino]acetyl]amino]-3-[[(5-methyl-1,3,4-thiadiazolyl)thio]methyl]-8-oxo-5-thia-1-azabicyclo[4.2.0]oct-2-ene-2-carboxylic acid, sodium salt 0.002 mole of the sodium salt product of Example 1 is brought into solution in 100 ml of a phosphate buffer at a pH of 6.4. Then 0.0024 mole of 5-methyl-1,3,4-thiadiazolyl-2-thiol is added. The solution is heated at 60° for six hours. After cooling, the pH is adjusted to 7.0 and the solution is chromatographed on the ion exchange resin Amberlite XAD-2. The fraction containing the desired product is freeze dried to yield [6R-[6α,7β(Z)]]-7-[[(2-amino-4-thiazolyl) [(1H-imidazol-2-yl-methoxy)imino]acetyl]amino]-3-[[(5-methyl-1,3,4-thiadiazolyl)thio]methyl]-8-oxo-5-thia-1-azabicyclo[4.2.0]-oct-2-ene-2-carboxylic acid, sodium salt.

EXAMPLES 42–47

Following the procedure of Example 41 but employing the cephalosporanic acid sodium salt shown in Col. I and the thiol shown in Col. II, one obtains the product shown in Col. III.

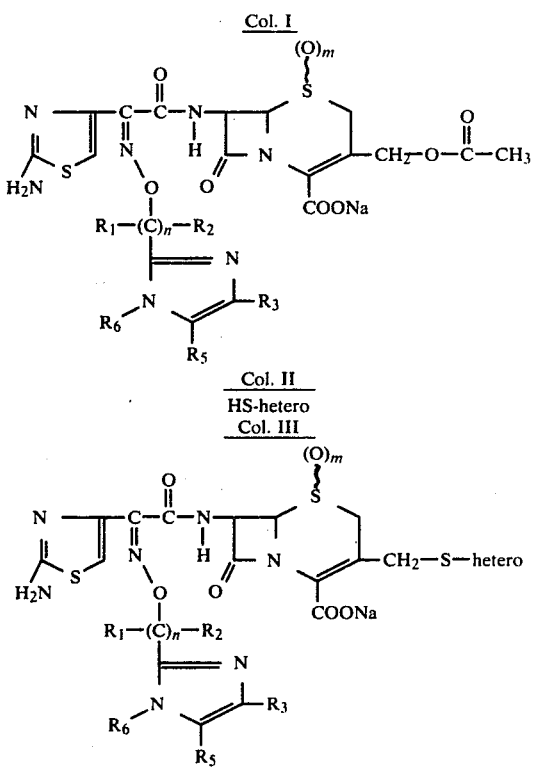

| Example | R₁ | R₂ | R₃ | R₅ | R₆ | m | n | hetero |
|---|---|---|---|---|---|---|---|---|
| 42 |  |  | —H | —H | —CH₃ | zero | zero | ![N—N with S, CH₃] |
| 43 | —CH₃ | —CH₃ | —CH₃ | —H | —CH₃ | two | one | ![N—N with S, CH₃] |
| 44 |  |  | —CH₃ | —H | —CH₃ | one | zero | ![N ring with N-C₂H₅] |
| 45 | —H | —H | —H | —H | —H | zero | one | ![N ring with N-CH₂SO₃Na] |

-continued

| Example | R₁ | R₂ | R₃ | R₅ | R₆ | m | n | hetero |
|---|---|---|---|---|---|---|---|---|
| 46 | | —H | —H | —H | —H | one | zero | 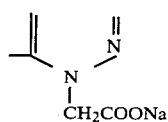 |
| 47 | —H | —H | —H | —CH₃ | —H | two | one | 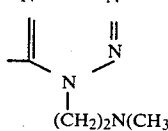 |

The products of Examples 42 to 47 are obtained in the syn or anti configuration depending upon the configuration of the 3-acetoxymethyl starting material shown in Col. I. Similarly, when m is one the compounds are obtained as the α- or β- sulfoxide depending upon the orientation of the 3-acetoxymethyl sulfoxide starting material. Also, when R₁ and R₂ are not the same, the products are obtained in the D-, L- or D,L-isomeric form depending upon the optical activity of the starting material shown in Col. I.

EXAMPLE 48

[5S[5α,6β,7α(Z)]]-3-[(Acetyloxy)methyl]-7-[[(2-amino-4-thiazolyl[(1H-imidazol-2-yl-methoxy)imino]acetyl-]amino]-8-oxo-5-thia-1-azabicyclo[4.2.0]oct-2-ene-2-carboxylic acid, 5-oxide sodium salt (β-sulfoxide, syn isomer)

The product of Example 2 can also be prepared by the following procedure.

1.69 g of [6R-[6α,7β(Z)]]-3-[(Acetyloxy)methyl]-7-[[(2-amino-4-thiazolyl) [(1H-imidazol-2-yl-methoxy)-imino]acetyl]-amino]-8-oxo-5-thia-1-azabicyclo[4.2.-0]oct-2-ene-2-carboxylic acid is obtained as in Example 1(e) is dissolved in 35 ml of methylene chloride and cooled to 0° C. 17 ml trifluoroacetic acid is added while stirring. 0.459 g of m-chloroperbenzoic acid is added and stirring is continued for 2.5 hours. The solvent is removed in vacuo and about 400 ml of ether is added. The precipitate is filtered off and washed with ether to yield 1.5 g of [5S]5α,6β,7α(Z)]]-3-[(acetyloxy)methyl]-7-[[(2-amino-4-thiazolyl[(1H-imidazol-2-yl-methoxy)imino]-acetyl]-amino]-8-oxo-5-thia-1-azabicyclo[4.2.-0]oct-2-ene-2-carboxylic acid, 5-oxide, trifluoroacetate salt having a melting point of 160° to 165° C.

This acid can be converted to its sodium salt by the procedure in Example 1(f).

EXAMPLES 49-57

Following the procedure of Example 48 the sulfides shown in Col. I can be oxidized to the β-sulfoxide shown in Col. II.

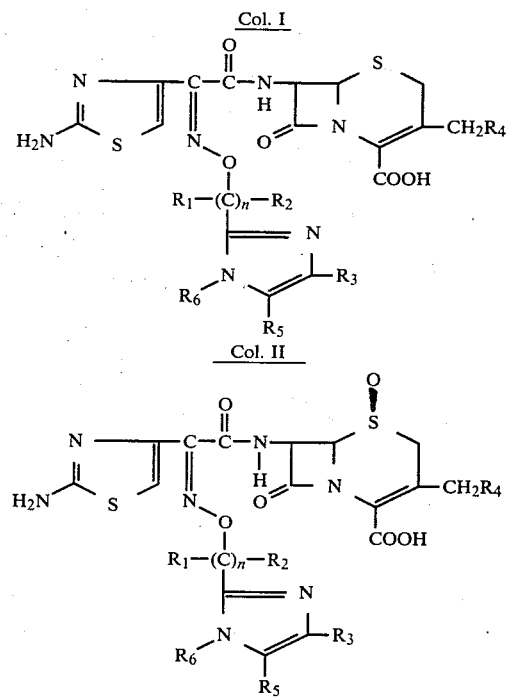

| Example | R₁ | R₂ | n | R₃ | R₅ | R₆ | R₄ |
|---|---|---|---|---|---|---|---|
| 49 | —H | —H | one | —H | —H | —CH₃ | —O—C(=O)—CH₃ |
| 50 | —H | —H | one | —CH₃ | —H | —CH₃ | -S-[tetrazolyl-N-CH₃] |
| 51 | | | zero | —H | —H | —H | -S-[tetrazolyl-N-CH₃] |

-continued

| Example | R₁ | R₂ | n | R₃ | R₅ | R₆ | R₄ |
|---|---|---|---|---|---|---|---|
| 52 | —CH₃ | —CH₃ | one | —H | —H | —CH₃ | 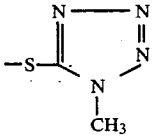 |
| 53 | —H | —H | one | —H | —H | —H |  |
| 54 | —H | —H | one | —H | —H | —CH₃ |  |
| 55 | —H | —H | one | —H | —H | —CH₃ |  |
| 56 | —H | —CH₃ | one | —H | —H | —CH₃ |  |
| 57 | —CH₃ | —CH₃ | one | —H | —H | —CH₃ |  |

The products of Examples 49 to 57 are obtained in the syn or anti configuration depending upon the configuration of the sulfide starting material shown in Col. I. Also, when $R_1$ and $R_2$ are not the same, the products are obtained in the D-, L- or D,L-isomeric form depending upon the optical activity of the starting material shown in Col. I.

The acid products of Examples 1 to 57 can also be converted to various ester forms (i.e., R is

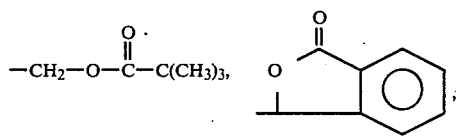

etc.) according to known procedures.

What is claimed is:

1. A compound of the formula

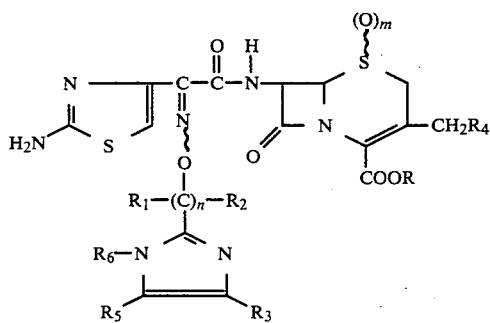

wherein

R is hydrogen, alkali metal,

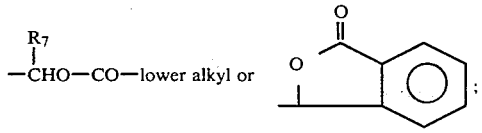

$R_1$ is hydrogen or methyl;
$R_2$ is hydrogen or methyl;
$R_3$ is hydrogen or methyl;
$R_4$ is hydrogen, —OCONH₂,

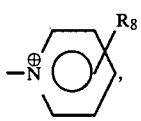

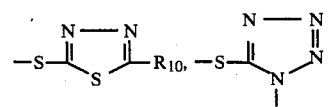

or —O—C(=O)—lower alkyl;

$R_5$ is hydrogen or methyl;
$R_6$ is hydrogen, methyl, benzyl or acetyl;
$R_7$ is hydrogen or lower alkyl;
$R_8$ is hydrogen or —CONH₂;
$R_9$ is hydrogen, lower alkyl,

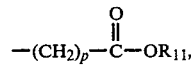

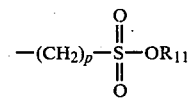

or —(CH₂)ₚ—N—(lower alkyl)₂;
$R_{10}$ is hydrogen or lower alkyl;
$R_{11}$ is hydrogen, sodium or potassium;
n is 1, 2, 3 or 4;
m is 0, 1 or 2;
p is 1, 2, 3 or 4.

2. The compound of claim 1 wherein the

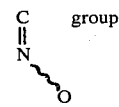 group is in the syn configuration;
n is one or two m is zero or one provided that when m is one the sulfoxide is in the β-configuration;

R is hydrogen, sodium, potassium,

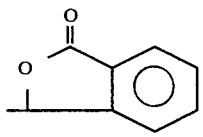

or —CH$_2$O—CO—lower alkyl;

R$_1$, R$_2$, R$_3$ and R$_5$ are independently selected from hydrogen and methyl;

R$_4$ is

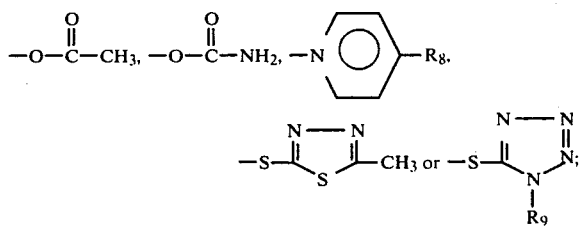

R$_6$ is hydrogen, methyl, benzyl or acetyl;
R$_8$ is hydrogen or

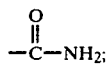

R$_9$ is hydrogen, methyl

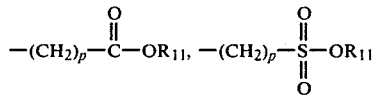

or (CH$_2$)$_p$—N(CH$_3$)$_2$;
R$_{11}$ is hydrogen, sodium or potassium and p is 1 or 2.

3. The compound of claim 2 wherein R$_4$ is

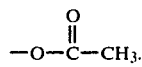

4. The compound of claim 3, [5S-[5α,6β,7α(Z)]]-3-[acetyloxy)methyl]-7-[[(2-amino-4-thiazolyl)[(1H-imidazol-2-yl-methoxy)imino]acetyl]amino]-8-oxo-5-thia-1-azabicyclo[4.2.0]oct-2-ene-2-carboxylic acid, 5-oxide, sodium salt.

5. The compound of claim 3, [6R-[6α,7β(Z)]]-3-[(acetyloxy)methyl]-7-[[(2-amino-4-thiazolyl)[(1H-imidazol-2-yl-methoxy)imino]acetyl]amino]-8-oxo-5-thia-1-azabicyclo[4.2.0]oct-2-ene-2-carboxylic acid, sodium salt.

6. The compound of claim 2 wherein R$_4$ is

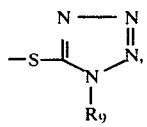

and R$_9$ is hydrogen or methyl.

7. The compound of claim 6, [6R-[6α,7β(Z)]]-7-[[-(2-amino-4-thiazolyl)[(1H-imidazol-2-yl-methoxy)imino]-acetyl]amino]-3-[[(1-methyl-1H-tetrazol-5-yl)thio]methyl]-8-oxo-5-thia-1-azabicyclo[4.2.0]oct-2-ene-2-carboxylic acid sodium salt.

8. An antibacterial pharmaceutical composition comprising a pharmaceutically acceptable carrier and an effective amount of one or more antibacterially active compounds of the formula

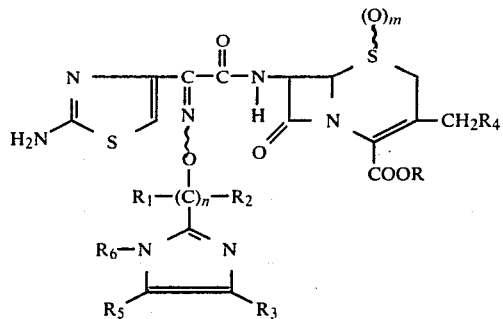

wherein
R is hydrogen, alkali metal,

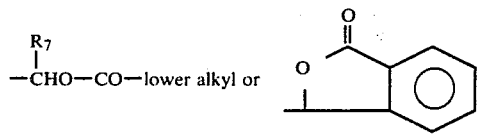

R$_1$ is hydrogen or methyl;
R$_2$ is hydrogen or methyl;
R$_3$ is hydrogen or methyl;
R$_4$ is hydrogen, —OCONH$_2$,

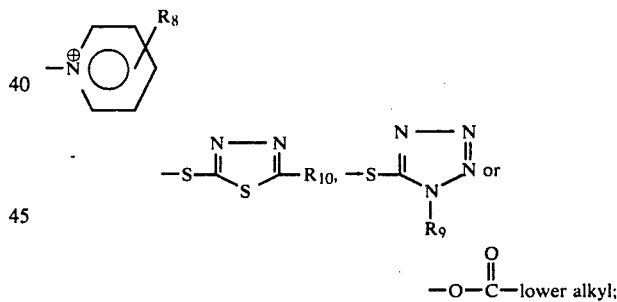

R$_5$ is hydrogen or methyl;
R$_6$ is hydrogen, methyl, benzyl or acetyl;
R$_7$ is hydrogen or lower alkyl;
R$_8$ is hydrogen or —CONH$_2$;
R$_9$ is hydrogen, lower alkyl,

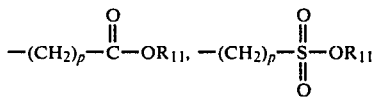

or —(CH$_2$)$_p$—N—(lower alkyl)$_2$;
R$_{10}$ is hydrogen or lower alkyl;
R$_{11}$ is hydrogen, sodium or potassium;
n is 1, 2, 3 or 4;
m is 0, 1 or 2;
p is 1, 2, 3 or 4.

9. The method of treating antibacterial infections in a mammalian specie which comprises internally administering an effective amount of the composition of claim 8.

10. The compound of claim 2, [5S-[5α,6β,7α(Z)]]-3-[(Acetyloxy)methyl]-7-[[(2-amino-4-thiazolyl)[1H-imidazol-2-yl-methoxy)imino]acetyl]amino]-8-oxo-5-thia-1-azabicyclo[4.2.0]oct-2-ene-2-carboxylic acid, 5-oxide, trifluoroacetate salt (1:1).

11. The compound of claim 2, [6R-[6α,7β(Z)]]-3-[(Acetyloxy)methyl]-7-[[(2-amino-4-thiazolyl)[(1H-imidazol-2-yl-methoxy)-imino]acetyl]amino]-8-oxo-5-thia-1-azabicyclo[4.2.0]oct-2-ene-2-carboxylic acid.

12. The compound of claim 6, [6R-[6α,7β(Z)]]-7-[-[(2-Amino-4-thiazolyl)[(1H-imidazol-2-yl-methoxy)imino]acetyl]amino]-3-[[(1-methyl-1H-tetrazol-5-yl)thio]methyl]-8-oxo-4-thia-1-azabicyclo[4.2.0]oct-2-ene-2-carboxylic acid, trifluoroacetate salt (1:2).

* * * * *